US010842477B2

(12) United States Patent
Barash

(10) Patent No.: US 10,842,477 B2
(45) Date of Patent: Nov. 24, 2020

(54) APPARATUS FOR OPENING AND HOLDING EYELIDS OPEN

(71) Applicant: Alexander Barash, Tzoran (IL)

(72) Inventor: Alexander Barash, Tzoran (IL)

( * ) Notice: Subject to any disclaimer, the term of this patent is extended or adjusted under 35 U.S.C. 154(b) by 23 days.

(21) Appl. No.: 16/400,751

(22) Filed: May 1, 2019

(65) Prior Publication Data

US 2019/0357897 A1 Nov. 28, 2019

(30) Foreign Application Priority Data

May 23, 2018 (IL) .......................................... 259549

(51) Int. Cl.
*A61B 17/02* (2006.01)
*A61B 90/50* (2016.01)

(52) U.S. Cl.
CPC .... *A61B 17/0231* (2013.01); *A61B 2090/502* (2016.02)

(58) Field of Classification Search
CPC ........... A61B 17/0231; A61B 2090/502; A61F 2009/0052; A61F 2009/0043; A61F 9/0026
USPC .......................................................... 606/236
See application file for complete search history.

(56) References Cited

U.S. PATENT DOCUMENTS

| | | | | |
|---|---|---|---|---|
| 1,230,873 A * | 6/1917 | Crossley | A61B 17/02 | 600/228 |
| 1,375,445 A * | 4/1921 | Crossley | A61F 9/007 | 600/233 |
| 4,988,183 A * | 1/1991 | Kasahara | A61B 3/113 | 351/158 |
| 5,433,190 A | 7/1995 | Sunalp | | |
| 6,224,546 B1 * | 5/2001 | Ramadan | A61B 17/0206 | 600/228 |
| 8,647,266 B2 | 2/2014 | Beck | | |
| 9,033,941 B2 * | 5/2015 | Rehkemper | A61F 9/0026 | 604/302 |
| 9,888,910 B2 | 2/2018 | Dahl | | |
| 2015/0088099 A1 * | 3/2015 | Lorch | A61F 9/0026 | 604/521 |

* cited by examiner

*Primary Examiner* — Jan Christopher L Merene
(74) *Attorney, Agent, or Firm* — Browdy and Neimark, PLLC

(57) ABSTRACT

An eye treatment apparatus for opening and holding eyelids of a patient open is described. The apparatus includes a supporting platform having a Y-type shape and including an upper beam configured for extending between a nose bridge and a forehead of the patient and for positioning on the forehead, a left leg and a right leg coupled to the upper beam, and configured for straddling a nose bridge of the patient and for positioning on patient's left and right cheeks, and a cross-arm mounted on the upper beam of the supporting platform. The apparatus also includes an opening assembly mounted on the cross-arm and configured for pulling an upper eyelid up for exposing an eye and retaining the eye of the patient in the open position. The also includes an adjustable annular band for placement around a head of the patient to secure the apparatus thereon.

20 Claims, 8 Drawing Sheets

APPARATUS FOR OPENING AND HOLDING EYELIDS OPEN

FIELD OF THE INVENTION

This invention relates to medical techniques for eye treatment, and in particular, to an eye treatment apparatus, where eye treatment is assisted by an eye opening assembly.

BACKGROUND OF THE INVENTION

Human eyes are susceptible to various forms of disease and distress, which may require eye treatment procedures, such as rinsing and/or administration of liquid medications, as well as diagnostic and examination procedures, such as intraocular pressure measurements, taking external ocular photos, fundus photos and other images used in optometry and ophthalmology. Eye treatment procedures usually require maintaining eyelids of the patient open to allow secure access to an eyeball for performing ocular examination and treatment.

A number of eye treatment devices have been proposed in the art for the purpose of holding eyelids of the patient open.

For example, U.S. Pat. No. 5,433,190 describes an eyelid speculum device used to hold a person's eyelids open for ocular surgery, treatment, examination, or some other reason. The device has two elongated arms, each arm having one free end. The other ends of the arms are attached to a joining member. A person may grasp gripping portions at the free ends of the arms, and move the arms toward each other until the gripping portions contact one another. The device may then be inserted between the upper and lower eyelids of a person's eye. The elongated arms engage the eyelids after the gripping portions are released. A substantial length of each arm engages the eyelids, because the arms are contoured to generally conform to the curvature and/or length of the eyelids.

U.S. Pat. No. 8,647,266 describes a speculum having first and second arms beginning at a proximal point and ending at a distal end and having a cup positioned at the distal end, an attachment portion positioned on the first arm and proximal to the cup, and a user manipulation element positioned within the attachment portion.

U.S. Pat. No. 9,888,910 describes an eyelid speculum for retracting a pair of eyelids. The eyelid speculum includes a first arm having a first blade portion contoured to generally conform to an eyeball globe and one of the pair of eyelids; a second arm having a second blade portion contoured to generally conform to the eyeball globe and the other of the pair of eyelids; and a mechanism carrying the first arm and the second arm. The mechanism is operable to hold the first arm and the second arm parallel to and in proximity to each other so that the first blade portion and the second blade portion may be inserted between the eyelids to engage said eyelids.

SUMMARY OF THE INVENTION

Despite the known techniques in the area of eye treatment, there is still a need for a novel apparatus for holding eyelids of the patient open that can be used in two related areas, such as clinical use and everyday use by an operator of the apparatus. In both these areas, the apparatuses for opening and retention of eyes being open during treatment is required, in order to render them easy to use and cost effective, so that these eye treatment apparatuses may be deployed to a large population.

It would be useful to provide an eye treatment apparatus, which allows for opening and retention of eyes being open in such a manner that the user need not place his/her fingers near the surface of the eyelids.

It would also be useful to provide an eye treatment apparatus, which allows for positioning or guiding the diagnostic and/or examination device to the desired position relative to the eye.

It would be advantageous to provide an eye treatment apparatus, that can be used by individuals having different facial features such as different width and height of the nose, or individuals having bulging eyes or eyes below a relatively normal position, thus avoiding the possible difficulty or inability in achieving an acceptable position of an apparatus in relation to an eye prior to eye treatment procedures.

The present invention satisfies the aforementioned needs in the art by providing a novel eye treatment apparatus for opening and holding eyelids of a patient during diagnostics and/or examination of eyes of a patient. The apparatus enables a user to place the apparatus on his/her face, and to align and stabilize an eye drop dispenser or any other diagnostic and/or examination device. The apparatus is equipped with an eye opening assembly enabling the treated eye to remain open while performing eye treatment in a relatively easy manner.

According to an embodiment of the present invention, the eye treatment apparatus for opening and holding eyelids of a patient includes a supporting platform having a Y-type shape. The supporting platform includes an upper beam, left leg and a right leg. The upper beam is configured for extending between eyebrows and a forehead of the patient and for positioning on an upper part of the forehead. The left and right legs are coupled to the upper beam, and are configured for straddling a nose bridge of the patient and positioning on left and right cheeks below corresponding lower eyelids of the patient.

The eye treatment apparatus also includes a cross-arm mounted on the upper beam of the supporting platform. The cross-arm is configured for displacing in both reciprocal directions along the upper beam.

The eye treatment apparatus also includes an opening assembly mounted on the cross-arm and displaceable in both reciprocal directions along the cross-arm. The eye opening assembly is configured for pulling an upper eyelid up for exposing an eye, and for retaining the eye of the patient in the open position.

The eye treatment apparatus also includes an adjustable annular band connected to the upper beam of the supporting platform. The adjustable annular band is configured for placement around a head of the patient to secure the apparatus thereon.

According to an embodiment of the present invention, the upper beam, the left and the right leg are terminated in corresponding feet configured for positioning on the forehead, left cheek and right cheek of the patient, correspondingly.

According to an embodiment of the present invention, the feet include cushion pads pivotally attached to the ends of the upper beam, the left leg and the right leg, correspondingly.

According to an embodiment of the present invention, the eye opening assembly includes an eyelid pulling frame including two frame arms having distal ends and separated at a predetermined distance. The eye opening assembly also includes an eyelid-retaining thread stretched between the distal ends of the frame arms. The eyelid-retaining thread is configured to follow an outer contour of the eyeball and conform to the shape of the eyeball when the eyelid-retaining thread is placed on the upper eyelid by applying a predetermined pressing force against the eye. For example, the predetermined pressing force is in the range of 0.5 N to 1.5N.

The eye opening assembly also includes a spring member configured to provide said predetermined pressing force to the eyelid pulling frame.

According to an embodiment of the present invention, the eyelid-retaining thread is a flexible filament having a predetermined strain.

According to an embodiment of the present invention, the spring member includes a strip spring. One end of the spring member is connected to the pulling frame, while the other end of the spring member is slidably connected to the cross-arm.

According to an embodiment of the present invention, the eye treatment apparatus for opening and holding eyelids further includes other opening assembly mounted on the cross-arm and displaceable in both reciprocal directions along the cross-arm. This other eye opening assembly is configured for pulling the other upper eyelid up for exposing the other eye, and for retaining the other eye of the patient in the open position.

According to an embodiment of the present invention, the eye treatment apparatus for opening and holding eyelids further includes other cross-arm mounted on the upper beam of the supporting platform. This other cross-arm is configured for displacing in both reciprocal directions along the upper beam.

According to an embodiment of the present invention, the eye treatment apparatus for opening and holding eyelids further includes a grasper assembly operatively connected to the other cross-arm. The grasper assembly is configured for holding an instrument for eye treatment. The instruments for eye treatment include, for example, a drop dispenser, an intraocular pressure recording device, a camera for images used in optometry and ophthalmology, or any other desired tools and instruments.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

LIST OF REFERENCE NUMERALS

Figure 1:
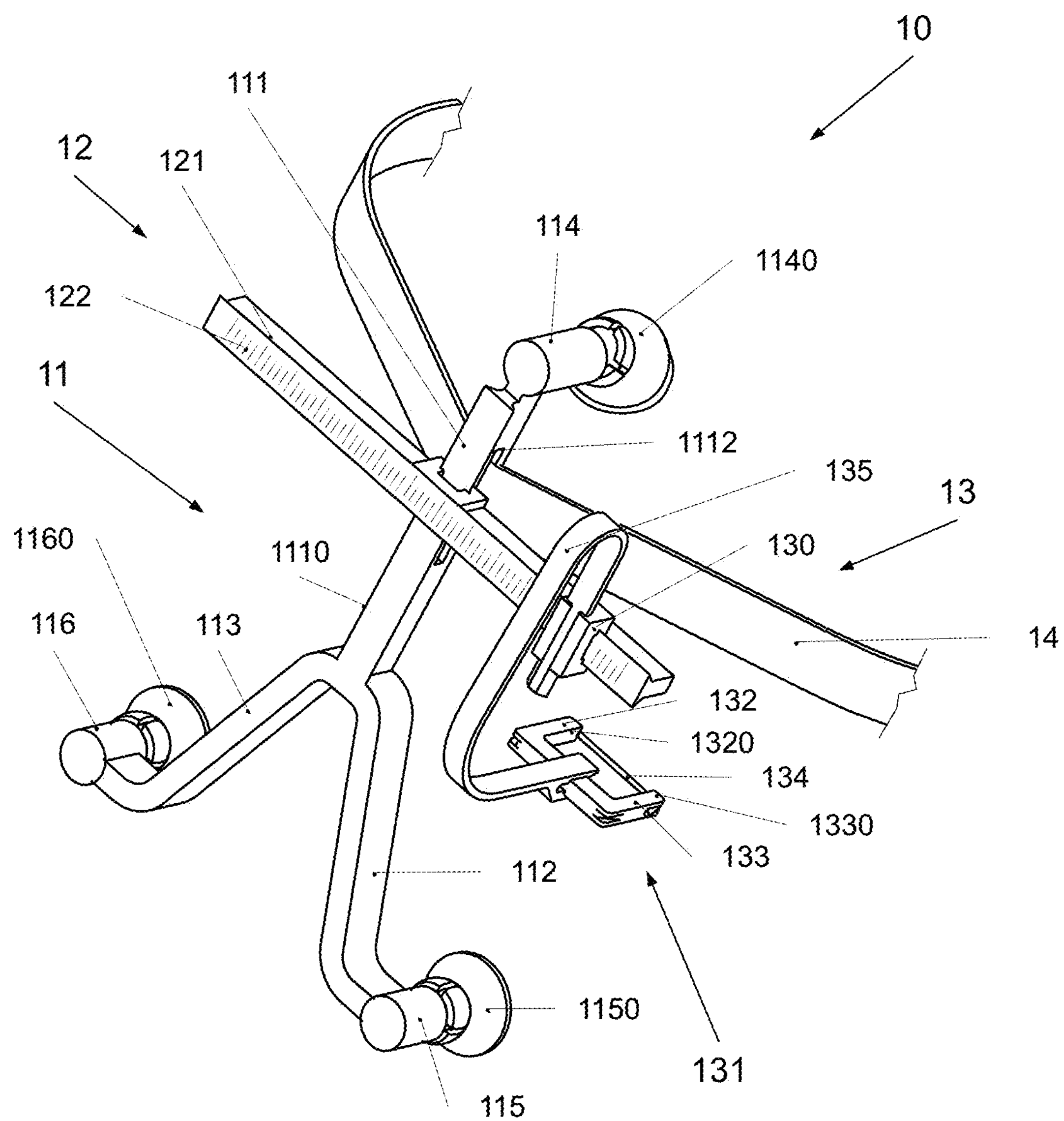
FIG. 1 illustrates an elevated perspective view of an eye treatment apparatus for opening and holding eyelids open, according to an embodiment of the present invention.

10, 40, 50, 60—eye treatment apparatus;
11—supporting platform;
110—lateral side;
111—upper beam;
112—left leg;
113—right leg;
114—upper foot;
115—left foot;
116—right foot;
1110—rail portion of the upper beam 111;
1112—slot;
12—cross-arm;
120—cross-arm carriage sleeve;
121—rail portion of the cross-arm 12;
13—eye opening assembly
130—opening assembly carriage sleeve;
131—eyelid pulling frame;
132, 133—frame arms;
134—eyelid-retaining thread;
135—spring member;
1320, 1330—distal ends of the frame arms 192, 193;
1352—one end of spring member 135;
1351—other end of spring member 135;
14—adjustable annular band;
15—other cross-arm;
16—grasper frame;
161—grasper assembly carriage sleeve;
162—grasper leg;
163—grasper frame;
164—hinge;
1631—delivery opening of the grasper frame 163;
20—nose bridge;
21—face;
22—patient;
23—eyes;
24—forehead;
25—cheeks;
26—nose bridge;
27—lower eyelids;
28—upper eyelids.

DETAILED DESCRIPTION OF EMBODIMENTS

The principles and operation of the eye treatment apparatus for opening and holding eyelids of a patient according to the present invention may be better understood with reference to the drawings and the accompanying description, it being understood that these drawings and examples in the description are given for illustrative purposes only and are not meant to be limiting. The same reference numerals and alphabetic characters will be utilized for identifying those components which are common in the eye treatment apparatus and its components shown in the drawings throughout the present description of the invention.

Figure 2:
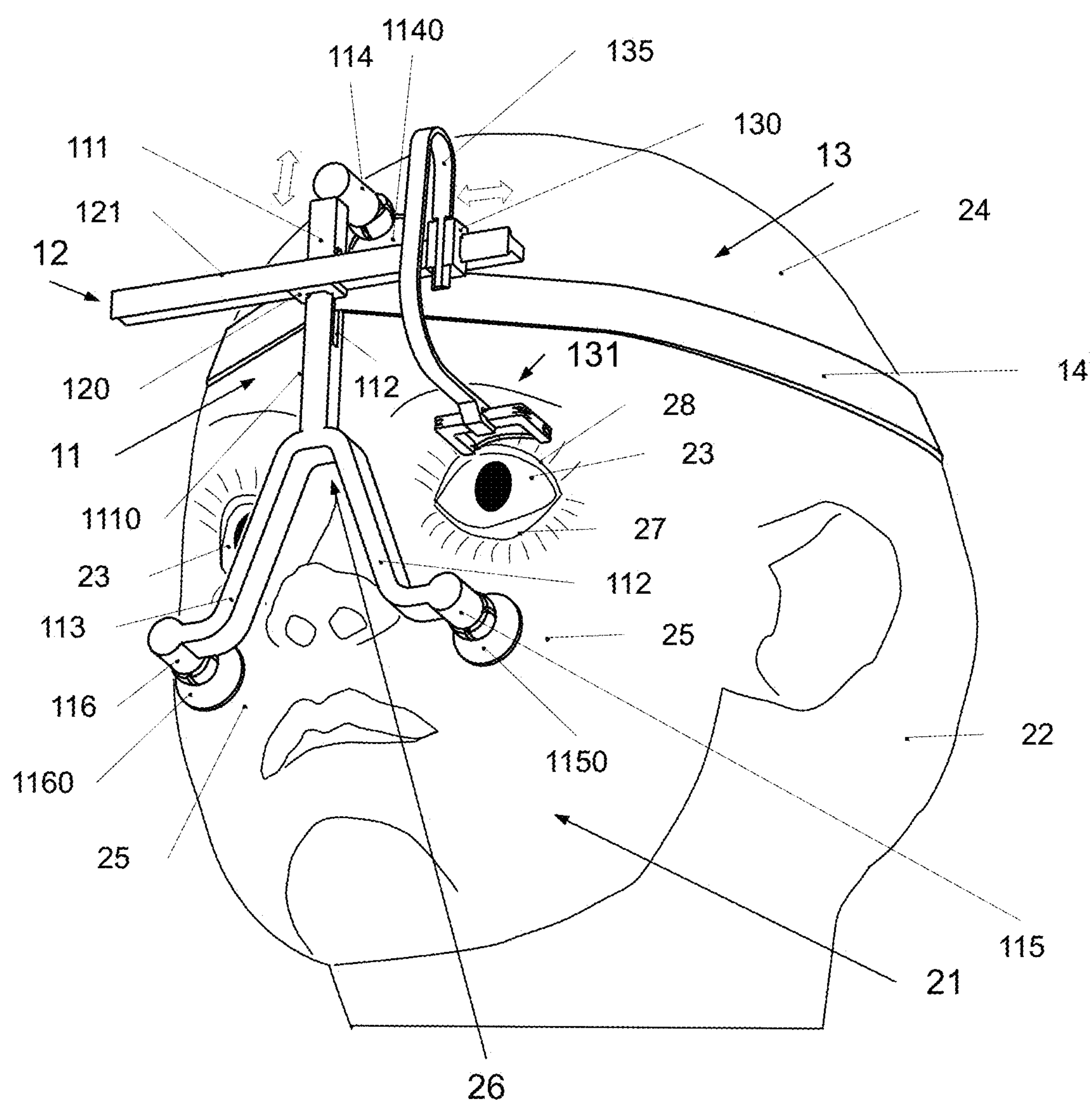
FIG. 2 illustrates a perspective view of the apparatus for eye treatment of FIG. 1 in use, according to an embodiment of the present application.

Referring to FIGS. 1 and 2 together, an elevated perspective view of an eye treatment apparatus 10, is illustrated in FIG. 1, according to one embodiment of the present invention. In turn, FIG. 2 illustrates a perspective view of the eye treatment apparatus 10 of FIG. 1 positioned on a face 21 of a patient 22 in use for opening and holding eyelids of the patient open 22 during diagnostics and/or examination of eyes 23 of the patient 22.

The eye treatment apparatus 10 for opening and holding eyelids of a patient includes a supporting platform 11 having a Y-type shape. The supporting platform 11 includes an upper beam 111 configured for extending between nose bridge 20 and a forehead 24 of the patient 22 and for positioning on the forehead 24.

The supporting platform 11 also includes a left leg 112 and a right leg 113 coupled to the upper beam 111 at their ends. The left leg 112 and the right leg 113 straddle a nose bridge 26 of the patient 22, and are positioned on left and right cheeks 25 below corresponding left and right lower eyelids 27 of the patient 22. It should be noted that the terms "upper beam", "left leg" and "right leg" are used herein for the purpose of description of a relationship between the different parts of the supporting platform 11 of the eye treatment apparatus 10 and a face 21 of the patient 22, as shown in FIG. 2, rather than for description of orientation of the eye treatment apparatus 10 in space.

According to an embodiment of the present invention, the upper beam 111, the left leg 112 and the right leg 113 are terminated in feet 114, 115 and 116, correspondingly. When desired, the feet 114, 115 and 116 include cushion pads 1140, 1150 and 1160, correspondingly. The cushion pads 1140, 1150 and 1160 can, for example, be made from polyester foam or ribbon.

Preferably, but not mandatory, the cushion pads 1140, 1150 and 1160 are separate elements that are pivotally attached to the ends of the feet 114, 115 and 116, correspondingly, for example, by using cylindrical or spherical hinges. The cushion pads 1140, 1150 and 1160 should have surface contact area with the patient's face sufficient for the cushion pads to gently engage with the skin of the patient and not cause significant discomfort to the patient during eye treatment procedures. For example, the surface contact area of the cushion pads 1140, 1150 and 1160 can be in the range of 3 $cm^2$ to 6 $cm^2$.

To further facilitate accurate eye treatment, the tactile surface of cushion pads 1140, 1150 and 1160 with the face of the patient 22 can be rough. This provision can provide desired friction between the tactile surface and the cheeks 25 of the patient 22 and assist the left leg 112 and the right leg 113 in retracting the lower eyelids 27 so as to expose the conjunctiva.

The dimensions of the upper beam 111, the left leg 112 and the right leg 113 of the supporting platform 11 and the distance between the feet 115 and 116 is in proportion to the typical dimensions of a human face. When desired, a set of the supporting platforms 11 having various dimensions can be manufactured and used to match diverse face sizes of patients.

The supporting platform 11 further includes a cross-arm 12 mounted on the upper beam 111 of the supporting platform 11. The cross-arm 12 can be displaceable along the upper beam 111 in both vertical reciprocal directions.

According to an embodiment of the present invention, the upper beam 111 includes a rail portion 1110, while the cross-arm 12 includes a cross-arm carriage sleeve 120 in the middle of the cross-arm 12. The cross-arm carriage sleeve 120 is placed on the rail portion 1110 such that the cross-arm 12 can slide along the rail portion 1110 of the upper beam 111 between the eyebrows 20 and the forehead 24 of the patient 22 in both vertical reciprocal directions. In order to provide secure fixation of the cross-arm 12 on the upper beam 111 in a desired place, the cross-arm carriage sleeve 120 can, for example, be equipped with a screw clamp (not shown) or with any other fixation mechanism.

The supporting platform 11 also includes an eye opening assembly 13 mounted on the cross-arm 12 and configured for pulling an upper eyelid 28 up for exposing an eye 23, and for retaining the eye 23 of the patient 22 in the open position. The opening assembly 13 can be displaceable along the cross-arm 12 in both reciprocal directions between the left and right sides of the patient's face 21.

According to an embodiment of the present invention, the supporting platform 11 and the cross-arm 12 are made from a light, resilient and pliable material. Examples of suitable materials include, but are not limited to, polymer, plastic or metal material.

According to an embodiment of the present invention, the cross-arm 12 includes a rail portion 121, while the opening assembly 13 includes an opening assembly carriage sleeve 130. The opening assembly carriage sleeve 130 is placed on the rail portion 121 such that the opening assembly 13 can slide along the rail portion 121 of the cross-arm 12 between the left and right sides of the patient's face 21 in both horizontal reciprocal directions. In order to provide secure fixation of the opening assembly 13 on the cross-arm 12 in a desired place, the opening assembly carriage sleeve 130 can, for example, be equipped with a screw clamp (not shown), or with any other fixation mechanism.

According to an embodiment of the present invention, the cross-arm 12 can include one or more length indicating marks 122, e.g., a scale, formed on an outer side of the cross-arm 12, visible to an operator of the apparatus 10. Such length indicating marks can assist to the operator to assign an appropriate position of the opening assembly carriage sleeve 130 on the cross-arm 12. These indicating marks can, for example, be formed as colored bands including grooves filled with a color material.

The eye opening assembly 13 is configured to pull an upper eyelid 28 up for exposing the eye 23 for treatment and retaining the eye 23 in the open position as long as required. According to the embodiment shown in FIGS. 1 and 2, the eye opening assembly 13 includes an eyelid pulling frame 131 including two frame arms 132 and 133 having distal ends 1320 and 1330 separated at a predetermined distance. For example, the predetermined distance between the distal ends 1320 and 1330 can be in the range of about 10 mm to 18 mm that corresponds to a value of about half to two-thirds of a horizontal size of an open eye of a patient (child or adult). As shown in FIGS. 1 and 2, the eyelid pulling frame 131 has a U-type shape, however, it can also have a V-type shape, or any other suitable shape.

The eye opening assembly 13 also includes an eyelid-retaining thread 134 stretched between the distal ends 1320 and 1330 of the frame arms 132 and 133. According to an embodiment, the eyelid-retaining thread 134 is a flexible filament having a predetermined strain that can follow an outer contour of the eyeball and conform to the shape of the eyeball when the eyelid-retaining thread 134 is placed on the upper eyelid 28 by applying a predetermined pressing force against the eye 23 along the line of contact of the eyelid-retaining thread 134 with the upper eyelid 28. For example, the predetermined pressing force can be in the range of about 0.5N (Newton) to 1.5N. Examples of materials suitable for the eyelid-retaining thread 134 include, but are not limited to, silicone, rubber and other flexible materials. According to an embodiment, the eyelid-retaining thread 134 can also be in the form of a thin coil spring.

In order to provide such pressing force, the eye opening assembly 13 of the eye treatment apparatus 10 includes a spring member 135 configured to provide the predetermined pressing force to the eyelid pulling frame 131. One end of the strip spring member 135 is connected to the pulling frame 131 by using a suitable connector, while other end of the strip spring member 135 is connected to (e.g., hooked to) the opening assembly carriage sleeve 130. In operation, the pressing force provided by the spring member 135 is transferred to the upper eyelid via the eyelid-retaining thread 134 in order to hold the upper eyelid open when the eyelid-retaining thread 134 is placed thereon.

According to the embodiments shown in FIGS. 1 and 2, the spring member 135 is in the form of a U-shaped strip spring that can, for example, be made from a spring steel material, however use of other materials and implementations of the spring member 135 are also contemplated. For example, the spring member 195 can be in the form of a spiral spring, a U-shaped rod, etc.

According to the embodiments shown in FIGS. 1 and 2, the eye treatment apparatus 10 also includes an adjustable annular band 14 connected to the upper beam 111 of the supporting platform. For connection of the adjustable annular band 14 to the upper beam 111, the upper beam 111 includes a slot 1112 and the adjustable annular band 14 passes through the slot 1112.

The adjustable annular band 14 is configured for removable placement around a head of the patient 22 to secure the eye treatment apparatus 10 thereon during the treatment procedure. The adjustable annular band 14 is made from a strong, elastic and resilient material, for example, from elastomer or rubber, and can be usable with different head sizes.

Figure 3A:
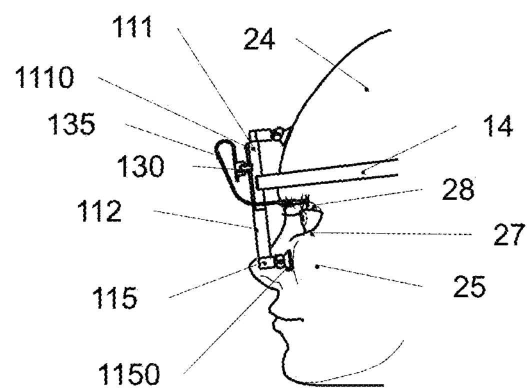
FIGS. 3A, 3B and 3C illustrate a method of use of the apparatus of FIG. 1, according to an embodiment of the present invention.
Figure 3B:
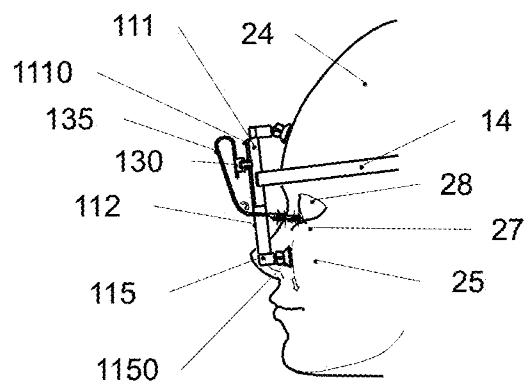
Figure 3C:
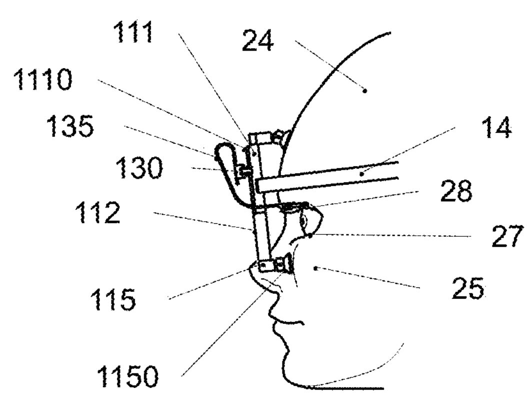

Referring to FIGS. 2, 3A, 3B and 3C together, a method of medical treatment of an eye of a patient by using the apparatus 10 is illustrated, according to an embodiment of the present invention. The method can be varied, and further steps may be added or deleted as appropriate, according to the medical circumstances. Although treatment of the patient's left eye is shown in FIGS. 3A-3C, generally, the eye 23 can be either the patient's left eye or right eye, mutatis mutandis.

First, the adjustable annular band 14 is adjusted to the appropriate size of the patient's head. The operator places the apparatus 10 over the user's face such that the cushion 1140 of the foot 114 is positioned on the user's forehead 24 while the cushions 1150 and 1160 of the left and right legs 115 and 116 are positioned on the corresponding user's cheeks 25. Then the operator places the adjustable annular band 14 around the patient's head and tightens the band to fix orientation of the apparatus 10 with respect to the patient's face 21. The orientation of the patient's head is then adjusted, as needed, to fit the particular patient and procedure. In particular, the patient 22 can maintain his/her head in a vertical position or may tilt the head backwards to take a horizontal position, as required.

As shown in FIG. 3A, the patient 22 may take a vertical position, and partially squint the eye under treatment. The operator moves the cross-arm 12 along the upper beam 111 and the opening assembly carriage sleeve 130 of the opening assembly 13 along the cross-arm 12 so that the eyelid-retaining thread 134 of the opening assembly 13 is located over the eye 23, and places the eyelid-retaining thread 134 onto the upper eyelid 27. Preferably, the eyelid-retaining thread 134 is positioned onto the upper eyelid 28 into a reference position that corresponds to a groove (not shown) that is associated with the upper eyelid sulcus.

Then, as shown in FIG. 3B, the spring element 135 is pulled away by the operator from the reference position, the patient closes the eye, and the eyelid-retaining thread 134 is lifted down to a predetermined distance, and positioned back on the upper eyelid 28 near the eyelashes to be stretched over the upper eyelid 28. This predetermined distance depends on the eye size and can be in the range of about 5 mm to 19 mm that corresponds to a value of the distance between the reference position and the edge of the upper eyelid in the closed position. In this state, the spring element 135 remains stretched.

Then, as shown in FIG. 3C, the operator releases the spring element 135, and the eyelid-retaining thread 134 returns to the reference position, thereby lifting the upper eyelid 28 up and opening the eye 23. The opened eye can be fixed in the open position as long as required for a particular eye treatment procedure.

In order to open and hold the lower eyelid 27 open, the left and/or right legs 112 and/or 113 can be lifted up from the cheeks 25 and the cheeks can be pulled down by the operator, thereby retracting the lower eyelids 27 so as to expose the conjunctiva. Then, the left and/or right legs 112 and/or 113 can be returned to the face to press against the cheeks.

Finally, the proper and appropriate medical procedure can be carried out, whether it is an administration of liquid medications, and/or diagnostic and examination procedures.

Figure 4:
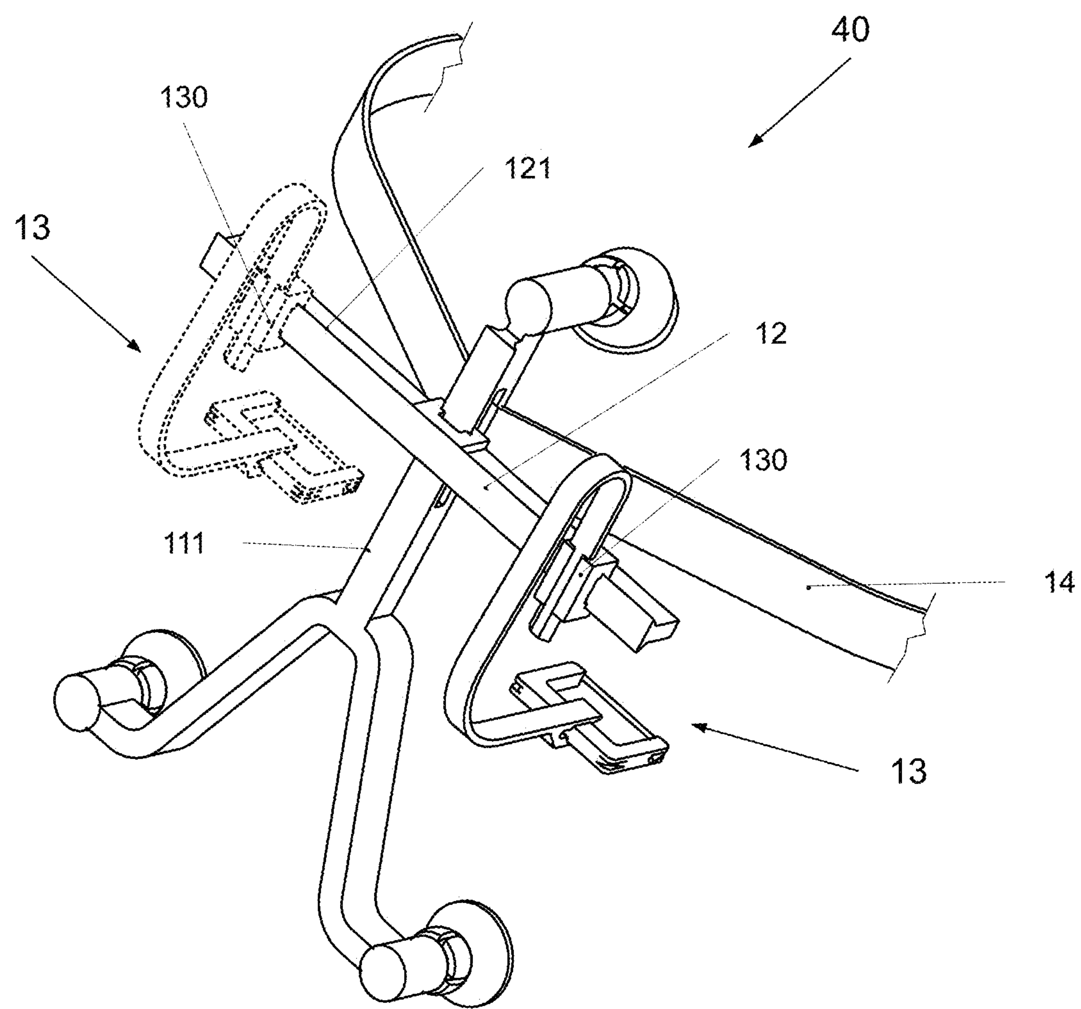
FIG. 4 illustrates an elevated perspective view of an apparatus for eye treatment, according to another embodiment of the present invention.

Referring to FIG. 4, an elevated perspective view of an eye treatment apparatus 40, is illustrated, according to another embodiment of the present invention. The eye treatment apparatus 40 shown in FIG. 4 is configured for opening and holding eyelids of both eyes open. Hence, the eye treatment apparatus 40 shown in FIG. 4 differs from the eye treatment apparatus 10 shown in FIG. 1 in the fact that it further includes other eye opening assembly 13 mounted on the cross-arm 12 and is displaceable in both reciprocal directions along the cross-arm 12. Such other eye opening assembly 13 eye opening assembly is configured for pulling other upper eyelid up for exposing other eye, and for retaining this eye of the patient also in the open position, when required.

Figure 5:
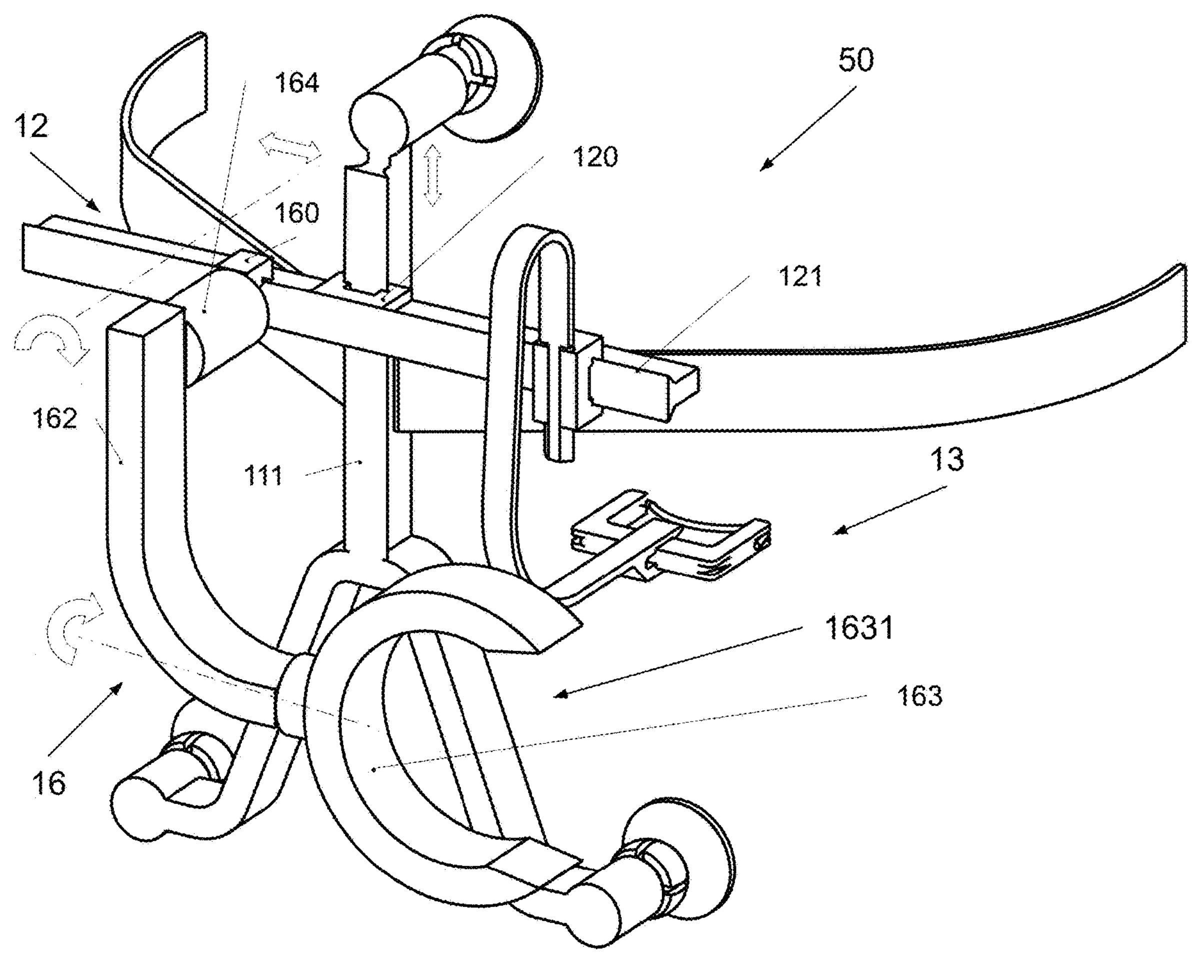
FIG. 5 illustrates an elevated perspective view of an apparatus for eye treatment, according to still another embodiment of the present invention.

Referring to FIG. 5, an elevated perspective view of an eye treatment apparatus 50, is illustrated, according to another embodiment of the present invention. The eye treatment apparatus 50 shown in FIG. 5 is configured for opening and holding eyelids open, and additionally for holding an instrument (not shown) for eye treatment.

Hence, the eye treatment apparatus 50 differs from the eye treatment apparatus 10 shown in FIG. 1 in the fact that it further includes a grasper assembly 16 mounted on and operatively connected to the cross-arm 12, and is displaceable in both reciprocal directions along the cross-arm 12. The grasper assembly 16 is configured for holding an instrument (not shown) for eye treatment.

According to an embodiment of the present invention, the grasper assembly 16 includes a grasper assembly carriage sleeve 160 placed on the rail portion 121 of the cross-arm 12 such that the grasper assembly 16 can slide along the rail portion 121 of the cross-arm 12 between the right side of the patient's face 21 and the eye opening assembly 13 in both horizontal reciprocal directions similar to the eye opening assembly 13.

In order to provide secure fixation of the grasper assembly 16 on the cross-arm 12 in a desired place, the grasper assembly carriage sleeve 160 can, for example, be equipped with a screw clamp (not shown) or with any other fixation mechanism.

The grasper assembly 16 includes a grasper leg 162 pivotably attached to a grasper assembly carriage sleeve 161 at one end, for example, by using a hinge 164. The grasper assembly 16 further includes a grasper frame 163 pivotably attached to the grasper leg 162 at other end of the grasper leg 162. The grasper frame 163 includes a delivery opening 1631 configured for grasping and holding an instrument for eye treatment (not shown). It should be understood that the configuration of the delivery opening 1631 shown in FIG. 5 can be used with various different types of medical instruments.

For example, the instrument may include a drop dispenser (not shown). The eye drop dispenser can include a container in the form of a bottle configured for holding medicament. The bottle can include a nozzle that allows liquid medicament to be ejected therefrom.

According to another example, the instrument may include an intraocular pressure recording device. According to still another example, the instrument can include a camera for images used in optometry and ophthalmology.

Figure 6:
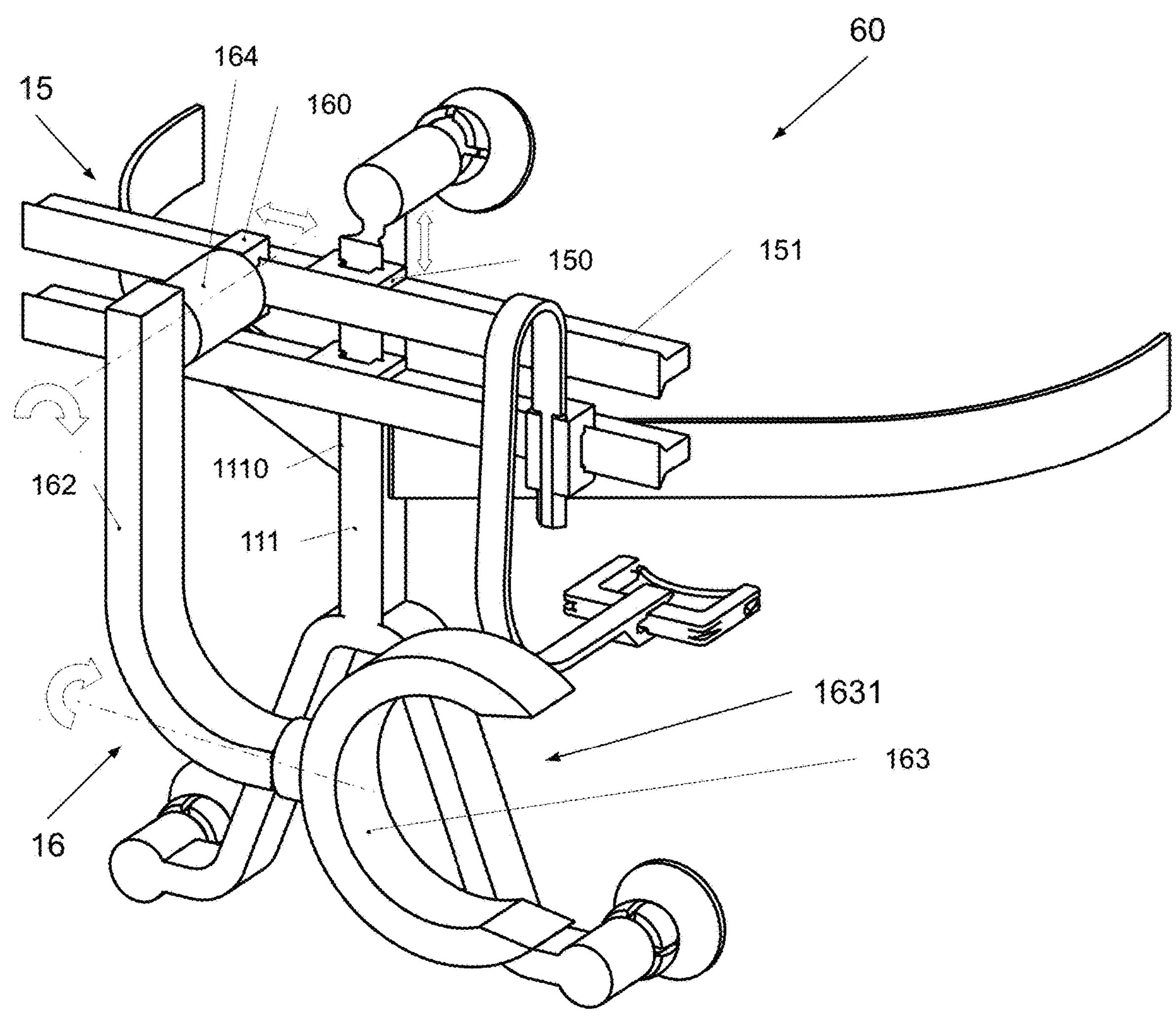
FIG. 6 illustrates an elevated perspective view of an apparatus for eye treatment, according to yet an embodiment of the present invention.

Referring to FIG. 6, an elevated perspective view of an eye treatment apparatus 60, is illustrated, according to still another embodiment of the present invention. The eye treatment apparatus 60 shown in FIG. 6 is configured for opening and holding eyelids open, and for holding an instrument (not shown) for eye treatment.

The eye treatment apparatus 60 differs from the eye treatment apparatus 50 shown in FIG. 5 in the fact that it further includes other cross-arm 15 mounted on the upper beam 111 of the supporting platform 11 and is displaceable along the upper beam 111 in both vertical reciprocal directions. In turn, the eye treatment apparatus 60 also differs from the eye treatment apparatus 10 shown in FIG. 1 in the fact that it further includes the grasper assembly 16 operatively connected to the other cross-arm 15 which is configured for holding an instrument (not shown) for eye treatment.

According to an embodiment of the present invention, the other cross-arm 15 includes other cross-arm carriage sleeve 150 in the middle of the other cross-arm 15. The other cross-arm carriage sleeve 150 is placed on the rail portion 1110 such that the other cross-arm 15 can slide along the rail portion 1110 of the upper beam 111 in both vertical reciprocal directions. In order to provide secure fixation of the other cross-arm 15 on the upper beam 111 in a desired place, the cross-arm carriage sleeve 150 can, for example, be equipped with a screw clamp (not shown) or with any other fixation mechanism. When desired the other cross-arm 15 can also include one or more length indicating marks, e.g., a scale (not shown), formed on an outer side of the other cross-arm 15, visible to an operator of the apparatus.

According to an embodiment of the present invention, the other cross-arm 15 includes a rail portion 151, while the grasper assembly 16 includes the grasper assembly carriage sleeve 160 placed on the rail portion 151 such that the grasper assembly 16 can slide along the rail portion 151 of the other cross-arm 15 between the left and right sides of the patient's face 21 in both horizontal reciprocal directions. In order to provide secure fixation of the grasper assembly 16 on the other cross-arm 15 in a desired place, the grasper assembly carriage sleeve 160 can, for example, be equipped with a screw clamp (not shown) or with any other fixation mechanism.

As described above, grasper assembly 16 includes a grasper leg 162 pivotably attached to a grasper assembly carriage sleeve 161 at one end, for example, by using a hinge 164. The grasper assembly 16 further includes a grasper frame 163 pivotably attached to the grasper leg 162 at other end of the grasper leg 162. The grasper frame 163 includes a delivery opening 1631 configured for grasping and holding an instrument for eye treatment (not shown). It should be understood that the configuration of the delivery opening 1631 shown in FIG. 6 can be used with various different types of medical instruments.

For example, the instrument may include a drop dispenser (not shown). The eye drop dispenser can include a container in the form of a bottle configured for holding medicament. The bottle can include a nozzle that allows liquid medicament to be ejected therefrom.

According to another example, the instrument may include an intraocular pressure recording device. According to still another example, the instrument can include a camera for images used in optometry and ophthalmology.

Figure 7:
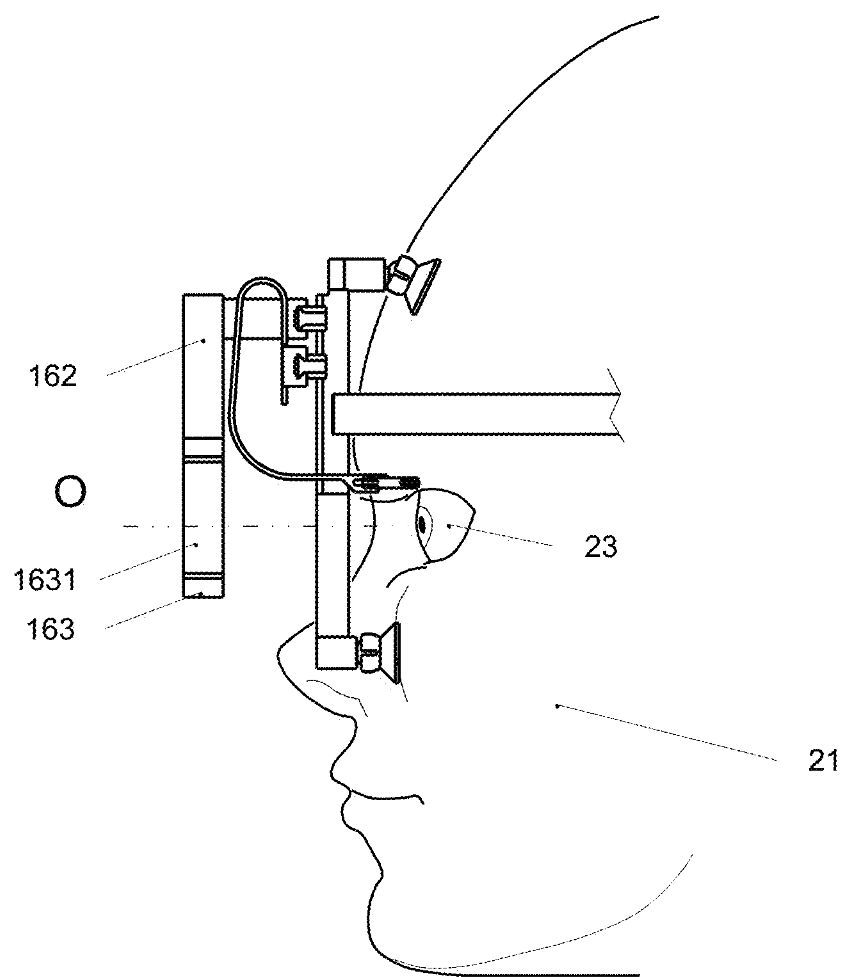
FIG. 7 illustrates a side view of an apparatus for eye treatment of FIG. 6 in use, according to an embodiment of the present application.

Referring to FIG. 7, a side view of an apparatus for eye treatment of FIG. 6 in use is illustrated, according to an embodiment of the present application. As shown in FIG. 7, the apparatus 60 is placed over the user's face such that an alignment axis O passes through the delivery opening 1631 of the grasper frame 163 and also passes through the eye 23.

Figure 8:
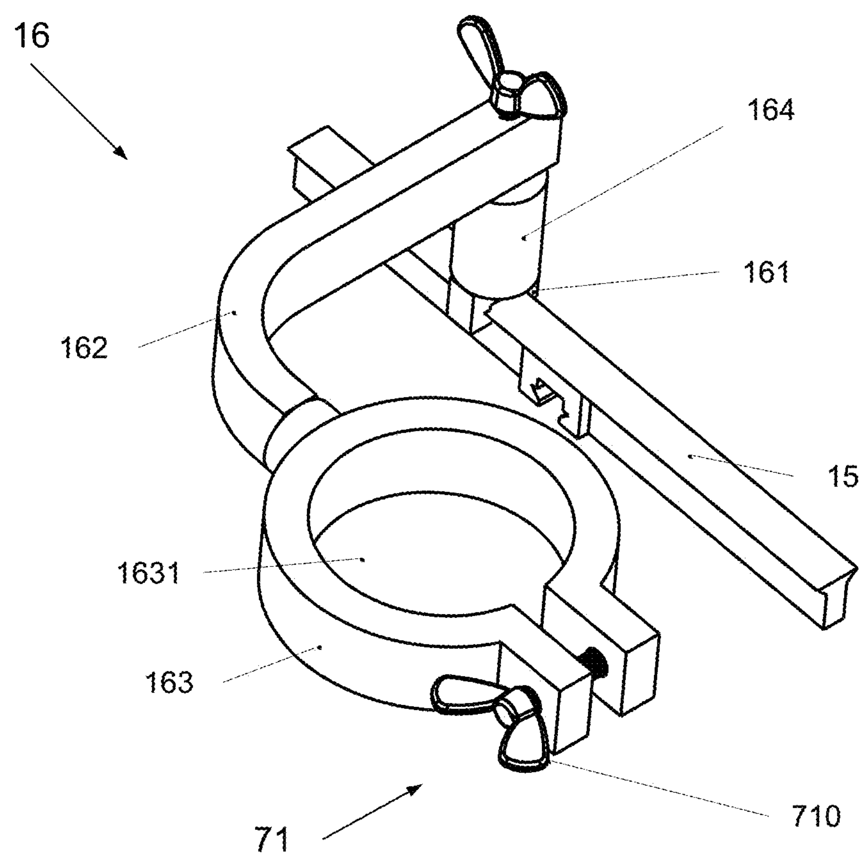
FIG. 8 illustrates an elevated perspective view of a grasping assembly of the eye treatment of FIGS. 5 and 6, according to an embodiment of the present invention.

Referring to FIG. 8, in order to provide secure grasping of the instrument within the delivery opening 1631, the eye treatment apparatus can include a locking mechanism 71 integrated with the grasping frame. As shown in FIG. 8, the locking mechanism 71 includes a screw clamp 710, however, other locking mechanisms are also contemplated.

Those skilled in the art to which the present invention pertains, can appreciate that while the present invention has been described in terms of preferred embodiments, the concept upon which this disclosure is based may readily be utilized as a basis for the designing of other structures, systems and processes for carrying out the several purposes of the present invention.

Also, it is to be understood that the phraseology and terminology employed herein are for the purpose of description and should not be regarded as limiting.

Finally, it should be noted that the words "comprising", "having" and "including" as used throughout the appended claims are to be interpreted to mean "including but not limited to".

It is important, therefore, that the scope of the invention is not construed as being limited by the illustrative embodiments set forth herein. Other variations are possible within the scope of the present invention as defined in the appended claims. Other combinations and sub-combinations of features, functions, elements and/or properties may be claimed through amendment of the present claims or presentation of new claims in this or a related application. Such amended or new claims, whether they are directed to different combinations or directed to the same combinations, whether different, broader, narrower or equal in scope to the original claims, are also regarded as included within the subject matter of the present description.

The invention claimed is:

1. An eye treatment apparatus for opening and holding eyelids of a patient open, the apparatus comprising:

- a supporting platform having a Y-type shape and including:

an upper beam configured for extending between a nose bridge and a forehead of the patient and for positioning on the forehead, and a left leg and a right leg coupled to the upper beam, and configured for straddling a nose bridge of the patient and for positioning on left and right cheeks below corresponding lower eyelids of the patient;

a cross-arm mounted on the upper beam of the supporting platform, and configured for displacing in both reciprocal directions along the upper beam;

an opening assembly mounted on the cross-arm and displaceable in both reciprocal directions along the cross-arm, said eye opening assembly being configured for pulling an upper eyelid up for exposing an eye, and for retaining the eye of the patient in the open position; and an adjustable annular band connected to the upper beam of the supporting platform, and configured for placement around a head of the patient to secure the apparatus thereon.

2. The eye treatment apparatus of claim 1, wherein the upper beam, the left and the right leg are terminated in corresponding feet configured for positioning on the forehead, left cheek and right cheek of the patient, correspondingly.

3. The eye treatment apparatus of claim 2, wherein the feet include cushion pads pivotally attached to the ends of the upper beam, the left leg and the right leg, correspondingly.

4. The eye treatment apparatus of claim 1, wherein said eye opening assembly includes:

an eyelid pulling frame including two frame arms having distal ends and separated at a predetermined distance;

an eyelid-retaining thread stretched between the distal ends of the frame arms, said eyelid-retaining thread configured to follow an outer contour of the eyeball and conform to the shape of the eyeball when the eyelid-retaining thread is placed on the upper eyelid by applying a predetermined pressing force against the eye; and a spring member configured to provide said predetermined pressing force to the eyelid pulling frame.

5. The eye treatment apparatus of claim 4, wherein the eyelid-retaining thread is a flexible filament having a predetermined strain.

6. The eye treatment apparatus of claim 4, wherein said spring member includes a strip spring.

7. The eye treatment apparatus of claim 4, wherein one end of the spring member is connected to the pulling frame, while the other end of the spring member is slidably connected to the cross-arm.

8. The eye treatment apparatus of claim 4, wherein said predetermined pressing force is in the range of 0.5 N to 1.5N.

9. The eye treatment apparatus of claim 1, wherein the cross-arm includes at least one length indicating mark formed on an outer side of the cross-arm visible to an operator of the apparatus.

10. The eye treatment apparatus of claim 9, wherein the indicating marks are formed as colored bands including grooves filled with a color material.

11. The apparatus of claim 1, further comprising an other opening assembly mounted on the cross-arm and displaceable in both reciprocal directions along the cross-arm, said other eye opening assembly being configured for pulling an other upper eyelid up for exposing other eye, and for retaining said other eye of the patient in an open position.

12. The apparatus of claim 1, further comprising a grasper assembly operatively connected to the cross-arm, and configured for holding an instrument for eye treatment.

13. The apparatus of claim 12, wherein said instrument includes a drop dispenser.

14. The apparatus of claim 12, wherein said instrument includes an intraocular pressure recording device.

15. The apparatus of claim 12, wherein said instrument includes a camera for images used in optometry and ophthalmology.

16. The apparatus of claim 1, further comprising an other cross-arm mounted on the upper beam of the supporting platform, and configured for displacing in both reciprocal directions along the upper beam.

17. The apparatus of claim 16, further comprising a grasper assembly operatively connected to said other cross-arm, and configured for holding an instrument for eye treatment.

18. The apparatus of claim 17, wherein said instrument includes a drop dispenser.

19. The apparatus of claim 17, wherein said instrument includes an intraocular pressure recording device.

20. The apparatus of claim 17, wherein said instrument includes a camera for images used in optometry and ophthalmology.

* * * * *